United States Patent [19]

Rust

[11] Patent Number: 4,918,024
[45] Date of Patent: Apr. 17, 1990

[54] METHOD FOR DETERMINATION OF DICYANODIAMIDE IN PLANTS OR PARTS OF PLANTS

[76] Inventor: Ulrich Rust, Pechleraustrasse 6, D-8223 Trostberg, Fed. Rep. of Germany

[21] Appl. No.: 268,212

[22] Filed: Nov. 3, 1988

[30] Foreign Application Priority Data

Nov. 13, 1987 [DE] Fed. Rep. of Germany ....... 3738675

[51] Int. Cl.$^4$ .............................................. G01N 33/00
[52] U.S. Cl. ................................... 436/106; 436/109; 436/161; 436/164; 436/177
[58] Field of Search ................. 436/20, 106, 109, 161, 436/164, 177

[56] References Cited

U.S. PATENT DOCUMENTS 4,692,415  9/1987  Rust ...................................... 436/20

FOREIGN PATENT DOCUMENTS 3625205  2/1987  Fed. Rep. of Germany ...... 436/161

OTHER PUBLICATIONS

Buyske et al., "Spectrophotometric Determination of Cyanamide", Analyt. Chem., 32, 1798–1800, 1960.
Nieman et al., "Reaction Rate Method for Determining Trace Concentrations of Cyanamide", Analyt. Chem., 48, 899–902, 1976.

Primary Examiner—Barry S. Richman
Assistant Examiner—Thalia P. Vassilatos
Attorney, Agent, or Firm—Kenneth P. Glynn

[57] ABSTRACT

The present invention is a method for determination of dicyanodiamide in a plant matrix, i.e. in a plant or a part of a plant. It involves a series of steps including extracting any dicyanodiamide from the plant matrix as well as purifying the dicyanodiamide obtained of interfering substances. Next, the dicyanodiamide obtained is reacted with 3-hydroxy-2-butanone in a non-aqueous, alcoholic hydrochloric acid medium to form 2-guanidino-4,5-dimethyloxazole, and then any 2-guanidino-4,5-dimthyloxazole formed is isolated using liquid-liquid extraction. Finally, any isolated 2-guanidino-4,5-dimethyloxazole is purified by reverse phase high pressure liquid chromatography (HPLC) and the amount of 2-guanidino-4,5-dimethyloxazole is determined spectrophotometrically at a wavelength of 260 nm.

20 Claims, 1 Drawing Sheet

METHOD FOR DETERMINATION OF DICYANODIAMIDE IN PLANTS OR PARTS OF PLANTS

BACKGROUND OF THE INVENTION

1. Field of the Invention

The present invention concerns a method for the determination of dicyanodiamide in plants or parts of plants, especially in cereals.

2. Prior Art Statement

The use of dicyanodiamide as a treatment material for plants is well known. For environmental protection reasons it is desirable to determine accurately the residual content of dicyanodiamide in these plants.

Up to now, analytical methods for the determination of small amounts of dicyanodiamide have been based either on photometric methods (cf. Zeitschrift Pflanzenernahrung Bodenkunde (J. Plant Nutrition Soil Science) 147, 268 (1984) or Landwirt. Forschung (Agricultural Research) 39, 20 (1986)) or on thin layer chromatographic methods (cf. CA 105, 178 074b).

In the photometric determination, the dicyanodiamide is detected by means of a color reagent, so that there is a problem with interfering impurities, especially when the determination must be undertaken in plants. The elimination of the plant matrix, as also in thin layer chromatographic methods, represents a problem that is solved only with difficulty, so that the sensitivity of detection and also the reproducibility are in no way satisfactory.

SUMMARY OF THE INVENTION

The present invention involves a method for determination of dicyanodiamide in a plant matrix, i.e. in a plant or a part of a plant. It involves a series of steps including extracting any dicyanodiamide from the plant matrix as well as purifying the dicyanodiamide obtained of interfering substances. Next, the dicyanodiamide obtained is reacted with 3-hydroxy-2-butanone in a non-aqueous, alcoholic hydrochloric acid medium to form 2-guanidino-4,5-dimethyloxazole, and then any 2-guanidino-4,5-dimethyloxazole formed is isolated using liquid-liquid extraction. Finally, any isolated 2-guanidino-4,5-dimethyloxazole is purified by reverse phase high pressure liquid chromatography (HPLC) and the amount of 2-guanidino-4,5-dimethyloxazole is determined spectrophotometrically at a wavelength of 260 nm.

BRIEF DESCRIPTION OF THE DRAWINGS

The present invention is more fully understood when the specification is taken in conjunction with the drawings appended hereto, wherein.

DETAILED DESCRIPTION OF THE PRESENT INVENTION

Figure 4:
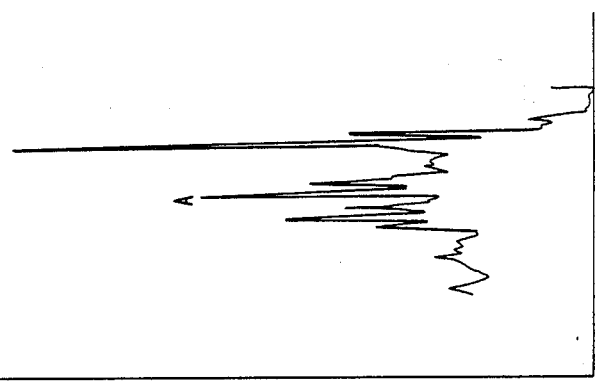

The present invention is therefore based on the task of developing a method for determination of dicyanodiamide in plants or parts of plants which does not display the disadvantages of the state of the art cited, but provides in a simple way a problem-free measurement method with high accuracy and sensitivity of detection which is in particular also suited to trace amounts.

This task, according to the invention, is solved by (a) extracting the dicyanodiamide from the plant matrix and purifying it from interfering substances (b) reacting it in non-aqueous alcoholic hydrochloric acid medium with 3-hydroxy-2-butanone (c) isolating the 2-guanidino-4,5-dimethyloxazole formed by means of liquid-liquid distribution (d) separating it by reverse phase high pressure liquid chromatography (HPLC) and (e) determining it spectrophotmetrically at a wave length of 260 nm.

Unexpectedly, it has been shown that dicyanodiamide can be determined by means of the invention method extremely specifically and sensitively even in plants or parts of plants.

According to the present invention, the plants or parts of plants, especially cereal grains, are ground up using standard equipment and the dicyanodiamide is isolated by extraction. In principle, all solvents in which dicyanodiamide has good solubility are suitable as extraction agents. Preferably, the solvent is a ketone, such as, for example, acetone or an alcohol such as methanol or ethanol, which are not only favorable in cost but because of their low boiling point can also be evaporated again easily. The solvent for the extraction can display a certain water content, which should not, however, exceed 50% by weight.

Since as a rule additional undesired hydrophobic impurities such as fats or waxes are dissolved in the extraction of the dicyanodiamide, a purification step is required before the derivative of the dicyanodiamide is formed.

For this purpose, the extraction medium is evaporated, the residue is taken up in water and then the hydrophobic impurities are separated out with a non-polar solvent while the dicyanodiamide remains in the aqueous phase. Non-polar solvents that can be used are hydrocarbons such as benzene, toluene or hexane, as well as halogenated hydrocarbons such as dichloromethane or chloroform, and also ethers such as diethyl ether.

The dicyanodiamide in the aqueous phase, after removal of the water by the usual methods, is reacted in non-aqueous alcoholic hydrochloric acid medium with 3-hydroxy-2-butanone to give the hydrochloride salt of 2-guanidino-4,5-dimethyloxazole. The reaction takes place at 25 to 65° C., especially at 40 to 50° C., in alcoholic hydrochloric acid medium in which the preferred alcohols are short-chain compounds such as ethanol or propanol. The concentration of hydrochloric acid in the alcoholic solution should be 200 to 800 mg, preferably 350 to 500 mg, HCl per liter of alcoholic solution, so as to avoid possible side-reactions.

It is self-evident that the quantity of 3-hydroxy-2-butanone added must be at least equimolar relative to the amount of dicyanodiamide to achieve a quantitative reaction. In practice, however, a 100- to 1000-fold excess of 3-hydroxy-2-butanone is recommended to achieve as rapid and complete a reaction as possible.

After the reaction is completed, the 2-guanidino-4,5-dimethyloxazole is present as the hydrochloride salt.

In order to achieve the separation of the free base, the reaction solution is neutralized, the alcoholic solvent removed, the residue taken up in an aqueous base and the 2-guanidino-4,5-dimethyloxazole is separated out with an organic solvent.

Aqueous bases that can be used are the usual lye solutions such as caustic soda or caustic potash, but also other aqueous salt solutions with an alkaline reaction by means of which a pH range of, preferably, 11.5 to 12.0 can be obtained.

Suitable organic solvents that can be used for the isolation of the 2-guanidino-4,5-dimethyloxazole from the alkaline aqueous phase are, in particular, chlorinated hydrocarbons such as dichloromethane or acetic acid esters such as ethyl acetate.

After the isolation of the oxazole, the organic solvent is completely removed, for example, in a rotary evaporator and the residue is taken up in the eluting agent planned for the high pressure liquid chromatography.

In the subsequent inverse phase high pressure liquid chromatography, preferably on a commercial C8 and C18 reverse phase (apparatus), the chromatographic separation is then realized.

The mobile phase used is preferably a mixture of sodium hexanesulfonate or octanesulfonate, water, methanol and an acid buffer, in which the quantity of sodium hexane- or octanesulfonate is usually between 0.1 and 2.0 per 1000 ml methanol/water buffer solution. The ratio of methanol to water to buffer solution can vary within wide limits, but mixtures of methanol/water/buffer solution of 300:650:50 to 600:350: 50 are regarded as preferred.

In general, those buffer solutions can be used as the acid buffers that display a pH of 2 to 5, with a citrate buffer with pH=3.0 having been shown to be especially advantageous.

The spectrophotometric determination of the 2-guanidino-4,5-dimethyloxazole is then realized at a wave length of 260 nm. The dicyanodiamide content can then be determined by evaluation of the height of the peak in comparison to a standard solution.

Using the invention method, the dicyanodiamide content can be determined simply and without difficulty with a lower detection limit of 10-100 ppb.

Figure 1:
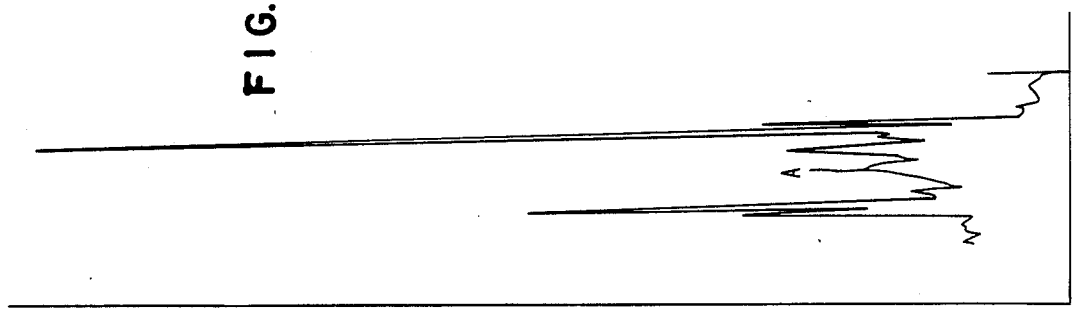
FIG. 1 shows an HPLC chromatogram for prior art untreated rise.

FIGS. 1 to 4 in the drawing show HPLC chromatograms that were obtained by the invention method. FIG. 1 shows an HPLC chromatogram that was obtained from untreated rice. No dicyanodiamide peak is to be seen, but only peaks that are due to substances contained in the plant.

Figure 2:
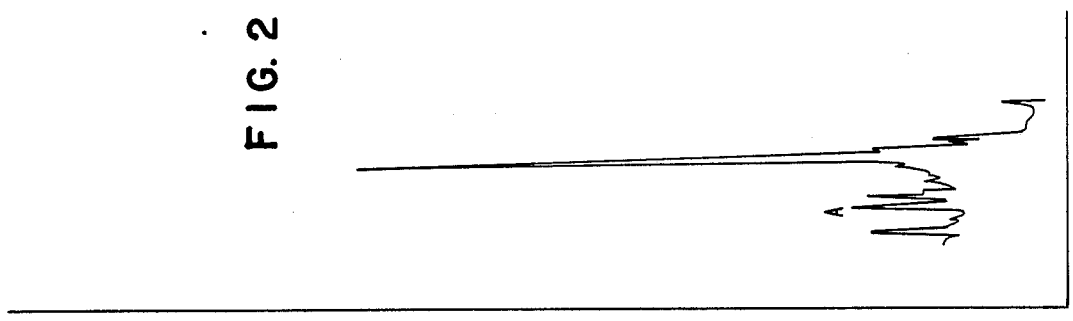
FIG. 2 illustrates an HPLC chromatogram for rice treated with 1.06 micrograms of dicyanodiamide.

FIG. 2 represents a chromatogram in which untreated rice was subsequently treated with 1.06 μg dicyanodiamide. Peak A corresponds to the dicyanodiamide peak.

Figure 3:
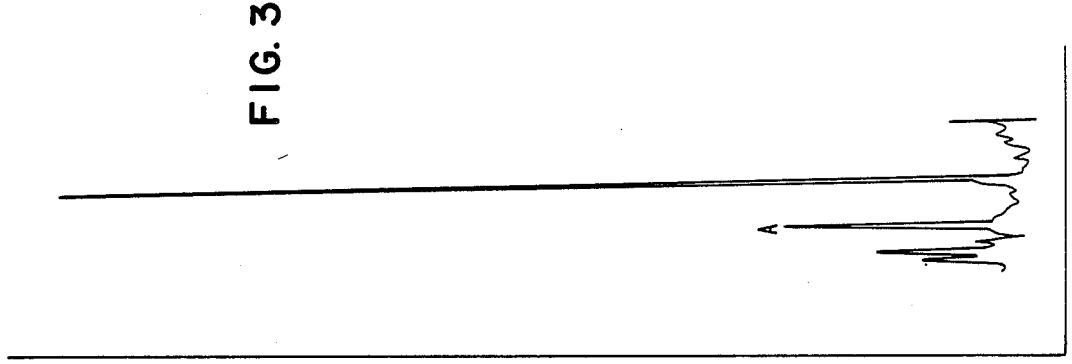
FIG. 3 shows an HPLC chromatogram of a standard solution of 2.12 micrograms dicyanodiamide; and, FIG. 4 illustrates an HPLC chromatogram of rice treated with 2.12 micrograms of dicyanodiamide.

FIG. 3 represents the chromatogram of a standard solution of 2.12 μg dicyanodiamide, where Peak A represents the dicyanodiamide peak.

FIG. 4, finally, shows the chromatogram of untreated rice subsequently treated with 2.12 μg (dicyanodiamide). It can be seen that the dicyanodiamide signal is twice as large as the signal in FIG. 2 and about the same in size as that in FIG. 3.

The following example will illustrate the invention more specifically.

EXAMPLE

1. Sample Preparation 50 g rice is carefully ground up in a coffee-grinder.

20 g of this is then slurried with 50 ml acetone and lixiviated for 10 min in an ultrasonic bath. It is filtered off and washed three times with 50 ml acetone each time. The acetone phase is evaporated to dryness in a rotary evaporator, the residue is taken up in water and washed into a sealable centrifuge receptacle. About 40-50 ml water are used for this. After addition of 30 ml diethyl ether, the mixture is shaken vigorously and centrifuged to separate the phases. The ether phase is filtered off and discarded. The aqueous phase is extracted again in the same way twice more with 30 ml ether each time and then evaporated to dryness in a rotary evaporator at a bath temperature of 40° C.

2. Formation of Derivative

The residue from 1. is taken up in 15 ml ethanol, treated with 2 mg 3-hydroxy-2-butanone in 5 ml ethanol and with 0.05 ml alcoholic hydrochloric acid and heated with stirring for 45 min at 45° C. It is cooled to room temperature, neutralized with ethanolic KOH against indicator paper and evaporated to dryness in the rotary evaporator. The residue is then dissolved in a total of 25 ml water and washed into a 100-ml separatory funnel. The solution is adjusted with caustic potash to a pH of 11.5 to 12.0 and then shaken five times with 25 ml dichloromethane each time. The solution is evaporated to dryness in a rotary evaporator at a bath temperature of 40° C. and the residue is taken up in 5 ml HPLC eluant.

3. Preparation of Standard

About 20 mg dicyanodiamide are weighed in a 100 ml measuring flask, dissolved in anhydrous ethanol and filled to the mark with ethanol. 1 ml of this solution is diluted with ethanol to 100 ml. 1 ml of this standard solution is converted to the derivative as described in point 2.

4. Chromatographic Conditions

HPLC system: Gilson Model 303 with rheodyne valve 7125 with 20 μl loop
UV detector: Uvicon 720 LC (Kontron)
Mobile phase: 1 g sodium hexanesulfonate is dissolved in 540 ml water and 400 ml methanol and treated with 60 ml buffer solution (citrate buffer of pH=3).
Separating acid; Partisil 5 C8, 250 mm (Whatman)
Temperature: room temperature
Flow: 0.6-1.0 ml
Wave length: 260 nm

5. Evaluation $$\text{ppm } DCD = (WS \cdot HSa)/(Wt \cdot HS)$$

ppm DCD=dicyanodiamide concentration in sample (mg/kg)
HSa=peak height of signal due to sample
HS=peak height of signal due to the standard
Wt=weight of sample (g)
WS=weight of dicyanodiamide used as standard (μg)

What is claimed is:

1. A method for the determination of dicyanodiamide in a plant matrix comprising:
   (a) extracting any dicyanodiamide from the plant matrix;
   (b) purifying any dicyanodiamide obtained in step (a) of any interfering substances;
   (c) reacting any dicyanodiamide obtained in step (b) with 3-hydroxy-2-butanone in a non-aqueous, alcoholic hydrochloric acid medium to form 2-guanidino-4,5-dimethyloxazole;

(d) isolating any 2-guanidino-4,5-dimethyloxazole formed in step (c) using liquid-liquid extraction;

(e) purifying any isolated 2-guanidino-4,5-dimethyloxazole of step (d) by reverse phase high pressure liquid chromatography; and, (f) determining spectrophotometrically at a wavelength of 260 nm the amount of 2-guanidino-4,5-dimethyloxazole obtained in step (e).

2. Method according to claim 1 wherein extraction of dicyanodiamide in step (a) is carried out using ketones and/or alcohols.

3. Method according to claim 2 wherein said ketones and/or alcohols contain up to 50% by weight of water.

4. Method of claim 1 wherein step (b) purification is accomplished by removal of hydrophobic impurities with a non-polar solvent from an aqueous dicyanodiamide phase.

5. Method of claim 2 wherein step (b) purification is accomplished by removal of hydrophobic impurities with a nonpolar solvent from an aqueous dicyanodiamide phase.

6. Method of claim 3 wherein step (b) purification is accomplished by removal of hydrophobic impurities with a non-polar solvent from an aqueous dicyanodiamide phase.

7. Method of claim 4 wherein said non-polar solvent is an ether or a hydrocarbon.

8. Method of claim 5 wherein said non-polar solvent is an ether or a hydrocarbon.

9. Method of claim 6 wherein said non-polar solvent is an ether or a hydrocarbon.

10. Method of claim 1 wherein step (c) occurs at 25-65° C.

11. Method of claim 10 wherein an excess of 100 to 1000 fold 3-hydroxy-2-butanone is added based on said dicyanodiamide.

12. Method of claim 1 wherein step (c) occurs at 40-50° C.

13. Method of claim 12 wherein an excess of 100 to 1000 fold 3-hydroxy-2-butanone is added based on said dicyanodiamide.

14. Method of claim 1 wherein said step (d) isolation is effected by liquid-liquid distribution in a two phase system consisting of alkaline aqueous solution and an organic solvent.

15. Method of claim 14 wherein said organic solvent is selected from chlorinated hydrocarbons and acetic acid esters.

16. Method of claim 1 wherein step (e) utilizes a C8 or C18 reverse phase method.

17. Method of claim 16 wherein a mixture of sodium hexanesulfonate or octanesulfonate and methanol/water/acidic buffer solution (ratio 300:650:50 to 600:350:50) is added as a mobile phase.

18. Method of claim 17 wherein 0.1 to 2.0 g sodium hexanesulfonate or octanesulfonate per 1000 ml methanol/water/acidic buffer solution is used.

19. Method of claim 17 wherein a citrate buffer of pH 3.0 is used as said acid buffer solution.

20. Method of claim 18 wherein a citrate buffer of pH 3.0 is used as said acid buffer solution.

* * * * *